United States Patent [19]
Latson et al.

[11] Patent Number: 5,861,003
[45] Date of Patent: Jan. 19, 1999

[54] APPARATUS AND METHOD FOR OCCLUDING A DEFECT OR APERTURE WITHIN BODY SURFACE

[75] Inventors: Larry A. Latson; John M. Kapitan, both of Shaker Heights, Ohio

[73] Assignee: The Cleveland Clinic Foundation, Cleveland, Ohio

[21] Appl. No.: 734,862

[22] Filed: Oct. 23, 1996

[51] Int. Cl.[6] .................................................. A61B 17/08
[52] U.S. Cl. ........................ 606/213; 606/215; 606/157
[58] Field of Search .................................. 606/213, 214, 606/215, 216, 151, 232, 220, 157; 623/12; 600/32; 128/898, 899, 887

[56] References Cited

U.S. PATENT DOCUMENTS

| | | | |
|---|---|---|---|
| 3,447,533 | 6/1969 | Spicer | 128/887 |
| 3,530,399 | 9/1970 | Erlebacher et al. | 606/213 |
| 3,874,388 | 4/1975 | King et al. | |
| 4,836,204 | 6/1989 | Landymore et al. | |
| 4,917,089 | 4/1990 | Sideris | |
| 5,108,420 | 4/1992 | Marks | |
| 5,171,259 | 12/1992 | Inoue | 606/213 |
| 5,284,488 | 2/1994 | Sideris | |
| 5,334,210 | 8/1994 | Gianturco | |
| 5,334,217 | 8/1994 | Das | |
| 5,342,393 | 8/1994 | Stack | 606/213 |
| 5,425,744 | 6/1995 | Fagan et al. | 606/213 |
| 5,433,727 | 7/1995 | Sideris | |
| 5,451,235 | 9/1995 | Lock et al. | 606/213 |
| 5,480,410 | 1/1996 | Cuschieri et al. | 606/213 |
| 5,531,759 | 7/1996 | Kensey et al. | |

OTHER PUBLICATIONS (1) Interventional cardiac catheterization in congenital heart disease–International Journal of Cardiology, 7 (1985) 1–11.
(2) Nonsurgical closure of patent ductus arteriosus: clinical application of the Rashkind PDA Occluder System—Circulation 75, No. 3, 583–592, 1987.
(3) Transcatheter umbrella closure of congenital heart defects—Circulation 75, No. 3, 593–599, Mar. 1987.
(4) Transcatheter Closure of Ventricular Septal Defects—Circulation 1988; 78:361–368.
(5) Atrial Septal Defect Occlusion with the Buttoned Device (a multi–Institutional US trial)—The American Journal of Cardiology—vol. 73, Feb. 1, 1994.
(6) Transvenous Atrial Septal Defect Occlusion by the Buttoned Device—The American Jounal of Cardiology, vol. 66, Dec. 15, 1990.
(7) Device for Transcatheter Closure of Intracardiac Defects—AJR 1993; 160:179–184.
(8) Double–Umbrella Closure of Atrial Defects. Circulation 1990; 82:751–758.
(9) Echocardiographic Follow–up of Atrial Septal Defect After Catheter Closure by Double–Umbrella Device. Circulation 1993; 88:621–627).

(List continued on next page.)

*Primary Examiner*—Michael Buiz
*Assistant Examiner*—Tina T.D. Pham
*Attorney, Agent, or Firm*—Calfee, Halter & Griswold LLP

[57] ABSTRACT

An apparatus and a method for occluding an aperture within a body surface, including an occlusion bag having a proximal sac and a distal sac, a delivery catheter, a guide catheter, a super-elastic wire, a release mechanism and a delivery sheath. The method of the invention includes affixing the delivery catheter to the proximal sac and then inserting the guide catheter into the delivery catheter. The super-elastic wire is attached to the release mechanism and the wire, release mechanism, occlusion bag, guide catheter and delivery catheter are inserted into a delivery sheath for transport to the aperture. After delivery, the occlusion bag is placed within the aperture and the wire is deployed within the bag. The bag and wire are repositioned if necessary, and the release mechanism is activated to release the wire. The guide catheter, delivery catheter, release mechanism and delivery sheath are then withdrawn.

7 Claims, 6 Drawing Sheets

OTHER PUBLICATIONS

(10) Prevalence of Patent Foramen Ovale In Patients With Stroke.—New England Journal of Medicine, vol. 318 No. 18.

(11) Simon Nitinol Inferior Vena Cava Filter: Initial Clinical Experience—Radiology 1989: 172:99–103.

(12) Nonsurgical Placement of Arterial Endoprosthese: A New Technique Using Nitinol Wire—Radiology 147: 261–263, Apr. 1983.

(13) Experimental Atrial Septal Defect Closure With a New, Transcatheter, Self–Centering Device—Circulation 1993;88 [part 1]: 1754–1764.

(14) Transcatheter Closure of Atrial Septal Defects—Circulation 1989; 79:1091–1099.

(15) Transcatheter Closure of Patent Foreamen Ovale After Presumed Paradoxical Embolism Circulation 1992;86:1902–1908.

(16) Nonoperative closure of atrial septal defects—Surgery, vol. 75 No. 3, Mar. 1997.

(17) Follow–up Results of transcatheter occlusion of atrial septal defects with buttoned device. Can J. Cardiol vol. 11 No. 8. Sep. 1995.

(18) Transvenous atrial septal defect occlusion in piglets with a "buttoned"double–disk device—Circulation 1990;81:312–318.

(19) Management of complications of Sideris transcatheter devices for atrial septal defect closure—The journal of Thoracic and Cardiovascular Surgery, Nov. 1993.

(20) Role of "buttoned" double–disk device in the management of atrial septal defects. ASD Closure vol. 123, No. 1.

(21) Monodisk: Device for Percutaneous Transcatheter Closure of Cardiac Septal Defects—Cardiovascular Intervent Radiology 1993; 16:308–312.

(21) Transcatheter Closure of Atrial Septal Defects Past, Present and Future—Circulation 1990; 82:1044–1045.

(22) Transcatheter Closure of Patent Foramen Ovale Therapeutic Overkill or Elegant Management for Selected Patients at Risk?

(23) Transcatheter Closure of Atrial Septal Defects: Hemodynamic Complications and Anesthetic Management—Anesth Analg. 1992;74:44–50. Transcatheter closure of atrial and ventricular septal defects—Herz 18 (1993), 135–142(Nr.2).

(24) Transcatheter Occlusion of Patent Ductus Arteriosus With Gianturco Coils—Circulation vol. 88, No. 4, Part 1 Oct. 1993. (25) Transcatheter Closure of Atrial Septal Defect and Patent Ductus Arteriosus–.

APPARATUS AND METHOD FOR OCCLUDING A DEFECT OR APERTURE WITHIN BODY SURFACE

FIELD OF THE INVENTION

The present invention generally relates to an apparatus and method for occluding a defect or aperture within a body surface, such as a wall separating two cavities. In particular, the present invention provides an apparatus for occluding apertures in which the apparatus is delivered through a catheter that allows for easy positioning, re-positioning, removal and even re-deployment of the apparatus to ensure proper placement and deployment.

BACKGROUND OF THE INVENTION

Septal defects generally refer to a perforation or hole passing through a septum. A septum is a thin wall of muscle separating two cavities. Atrial septal defects ("ASD") are a common congenital cardiac abnormality. A large atrial septal defect can lead to enlargement of the right atrium and right ventricle. Also, a large atrial septal defect may require closure to prevent these complications. To close an ASD, open heart surgery has been used for decades. In such an operation, the patient's chest must be opened and heart temporarily bypassed. Then, the surgeon sutures the defect shut or if the defect is too large, a patch of biocompatible material is sewn in place to close the aperture.

In order to avoid the trauma and complications caused by open heart surgery, transcatheter techniques to close septal defects have been attempted. These techniques deliver an occlusion device through a catheter to the septal defect. The device is placed into the defect and permanently deployed.

A number of such transcatheter devices have been described. King et al. proposed such a device in U.S. Pat. No. 3,874,388. The King apparatus comprises a pair of complicated umbrellas. Each umbrella frame is made of stainless steel with each frame having six ribs to maintain each umbrella in an open position. Also the King apparatus has barbs at the ends of each rib to anchor the apparatus to the surrounding tissue. While the King apparatus marked an improvement over open-heart surgery, the umbrellas are difficult to unfold after passage through a catheter. Moreover, repositioning of the apparatus is almost impossible as the barbs prevent movement once they are anchored to the tissue. Finally, due to the large size of the device and its delivery catheter (23 French), the device is not appropriate for use with small children.

Another device, the Rashkind occluder provides a single umbrella closure apparatus with a delivery system which permitted use in small children. Rashkind's apparatus is a single disk umbrella–type closure device with barbed hooks similar to those of King. Rashkind deploys the single umbrella within the left atrium and then positions it against the left side of the atrial septum. As with King, the barbed hooks prevent disengagement of the device upon deployment. This results in poor centering capabilities and no re-positioning or removal.

Lock, et al., developed a "modified" double-umbrella occlusion apparatus. Lock's apparatus resembles a clamshell which is well known in the art. The arms of Lock's "clamshell" device are hinged to allow them to fold back against themselves. Also Lock's device is more compact than its predecessor's as it allows delivery in children weighing as little as 8 kilograms.

Sideris proposed an occlusion apparatus that combined a single umbrella occluder with a separate anchoring device. This invention is shown in U.S. Pat. No. 4,917,089. Sideris'apparatus utilized a series of ribs to support an umbrella. A string connects the arms of the umbrella to a rhomboidally shaped anchor. This anchor includes an internal wire skeleton and a central piece of rubber. The anchor is positioned opposite the umbrella with a length of string limiting the movement of the device.

Marks, in U.S. Pat. No. 5,108,420, discloses is an occlusion apparatus in which a wire frame is folded and delivered to the aperture via a catheter. Marks uses a shape-retaining alloy such as nitinol to form its wire frame. Upon delivery, the wire is allowed to unfold to yield two planar members. The wire frame may be covered with a membrane or the frame by itself may occlude the aperture. The Marks apparatus is made from a thermal formulation of shape retaining nitinol alloy. This thermal formulation nitinol is difficult to generate within the appropriate transition temperature range (TTR) for the human body. Formulation of this nitinol is difficult because the range between full deployment at body temperature and zero deployment at room temperature is only 17° C. To prevent early deployment of the frame during delivery, Marks infuses the catheter delivery system with a cool, saline bath in an attempt to keep the wire at room temperature during transport to the aperture.

Besides the above-mentioned delivery complications encountered by Marks, the structural integrity of the frame is less than desirable. The frame has multiple arms attached to a central loop and extending radially from this loop. Due to this multiple wire arm configuration, the arms might easily break at their connection point as the wire arms bear the majority of the stresses placed on the apparatus. Also, due to this configuration, the Marks apparatus does not resist loading well.

Marks also teaches that a membrane should be attached to the wire or the wires should be embedded in this membrane. By having an attached or embedded membrane, the wire may not be used to re-position the occluding device once deployed. In other words, Marks device is cumbersome because the wire cannot be manipulated within the membrane. Furthermore, since Mark's wire is body temperature activated, once deployed, it cannot be re-folded and withdrawn if not positioned properly.

Das, in U.S. Pat. No. 5,334,217, proposed an occlusion apparatus having a pair of disks. Each disk is attached to a wire frame with each wire frame being formulated of a shape retaining alloy in a super-elastic formulation. Das forms each frame from a single strand of wire. The wire is twisted to form a plurality of legs with the ends of the wire connected to each other. The device is folded upon itself and forced into a catheter for delivery. Once the catheter has reached the aperture, the distal frame is pushed out of the catheter and expanded into the cavity distal to the aperture. Then, the other frame is allowed to expand in the cavity proximal to the aperture. Also, Das attaches a membrane to each portion of the frame so the wire frame may not be independently removed and the device cannot be readily collapsed back into the delivery catheter to be removed or repositioned. Thus, an occlusion device with repositioning and retrieval capabilities is desirable.

SUMMARY OF THE INVENTION

This invention includes an apparatus and method for occluding an aperture. The apparatus is adapted to be delivered to the aperture by a catheter system. The catheter system has positioning and re-deployment capabilities. The invention includes a super-elastic wire frame preprogrammed to assume a desired shape when tension upon the wire frame is released. Furthermore, the collapsible wire frame is designed to be movably disposed within an occlusion bag. Due to this frame design, the occlusion apparatus can be repositioned, redeployed and even removed from the aperture after deployment. Preferably, the bag has a "figure-eight" or dumbbell shape composed of two disk-shaped sacs with the sacs joined at their respective centers by attaching the sacs to a coil of radio-opaque material.

The occlusion apparatus delivery system is comprised of multiple catheters coupled with a release system to separately release the wires and sacs. A guide catheter is disposed within the occlusion bag with the super-elastic wire frame contained within the guide catheter for delivery to the aperture. The guide catheter is then placed within a delivery catheter with the delivery catheter connected to the proximal portion of the occlusion bag's proximal sac. Then, this entire assembly is disposed within a delivery sheath. The delivery sheath and its contents are then delivered to the aperture.

The sheath is placed at the distal portion of the aperture. The distal sac is then advanced out of the sheath and into the cavity distal to the aperture. The distal portion of the wire is forced out of the guide catheter to assume its programmed shape within the distal sac.

Once the distal sac and distal wire are in proper position, the entire assembly is gently pulled back to allow the distal sac and distal wire to rest against the distal side of the atrial septum. The delivery sheath is then withdrawn to expose the proximal sac. The guide catheter is then withdrawn into the proximal sac and the proximal wire is advanced to assume its preprogrammed shape within the proximal sac.

Up to this point, the entire assembly may be entirely withdrawn into the sheath for repositioning, removal or redeployment. Once the device is in proper position, the release mechanism is activated to release the wire. The release mechanism and guide catheter may be withdrawn entirely through the delivery catheter. The delivery catheter is then disconnected from the proximal sac and the entire remaining assembly withdrawn, leaving the device in place to occlude the aperture.

DETAILED DESCRIPTION OF THE INVENTION

The invention includes an apparatus and method for occluding apertures in body walls or membranes. The apparatus is adapted to be delivered through the body by a catheter system to the aperture. One such aperture which this invention can occlude is an atrial septal defect. Atrial septal defect is a common congenital cardiac abnormality that is the type of aperture for which the preferred embodiments of the invention are designed, but this invention may be used to occlude other apertures such as ventricular septal defects, patent foreman ovale, patent ductus arteriosus or apertures in the fallopian tubes.

Frequently, surgical closure of these defects is the only available option to correct a defect in a septal wall. Reliable, safe occlusion devices, such as the present invention, are needed to close such apertures without resorting to surgery. Furthermore, easy positioning, adjusting and withdrawal of occlusion devices during their method of delivery is desirable and needed.

Figure 1:
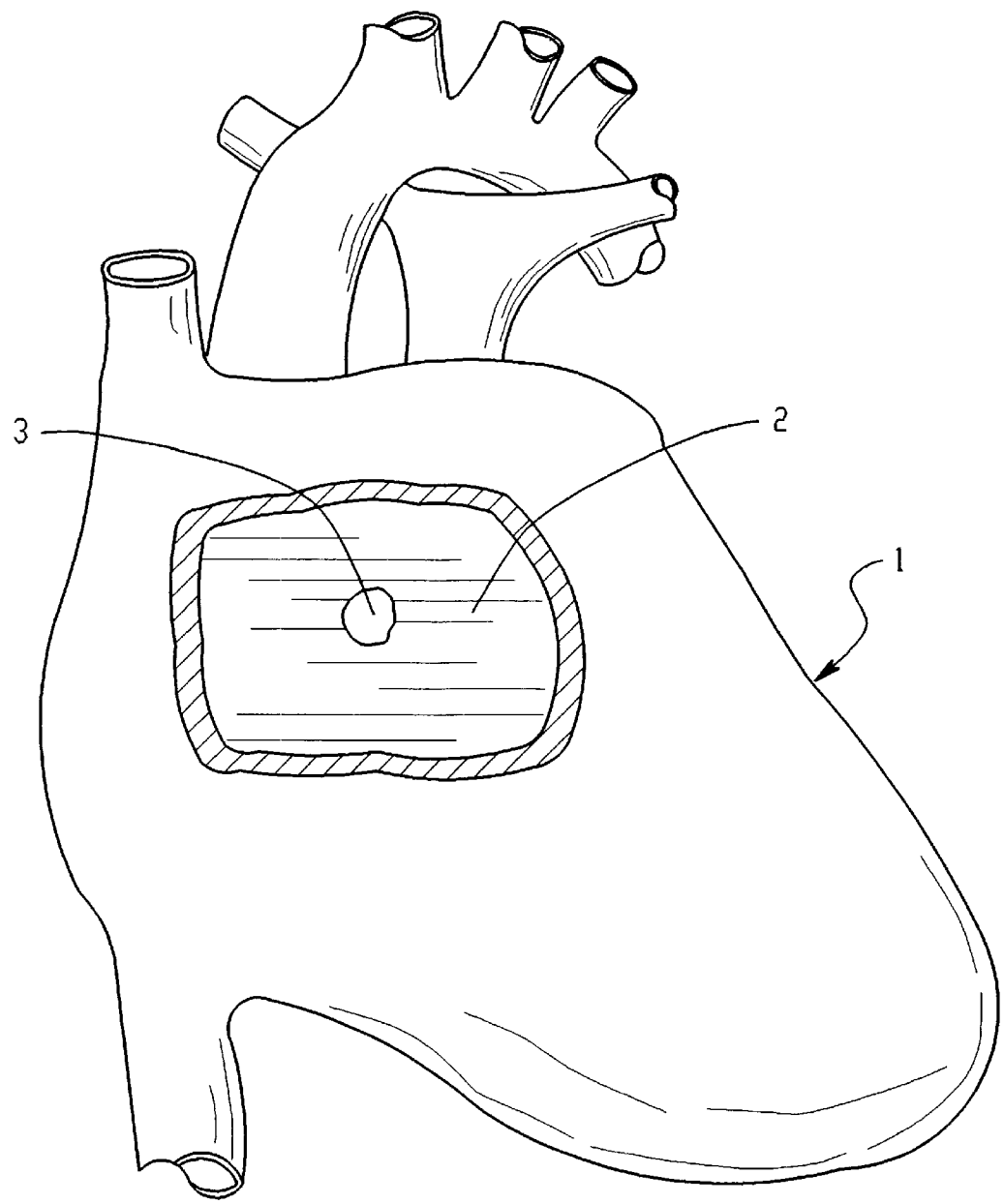
FIG. 1 is a schematic partially cut-away view of a heart with an atrial septal defect.

FIG. 1 schematically illustrates a heart 1 having an atrial septum 2 dividing the two atria with an atrial septal defect (ASD) 3 extending through the atrial septum 2. As shown in FIG. 1, a large ASD 3 can cause enlargement of the right atrium and decrease life expectancy as blood shunts from the left to right atrium and ultimately to the lungs via the right ventricle and pulmonary arteries. In addition to the percentage of the population with a large ASD, an estimated 15% of the entire population has a small atrial septal defect or patent foreman ovale (PFO). Patients with a PFO do not show the hemodynamic consequences that patients with a large ASD show, but they may be at risk for intermittent right to left shunting. This shunting can allow passage of a venous thromboembolus directly to the left side of the heart and into cerebral circulation. Mounting evidence exists that PFO should be considered a risk factor for stroke.

Figure 2:
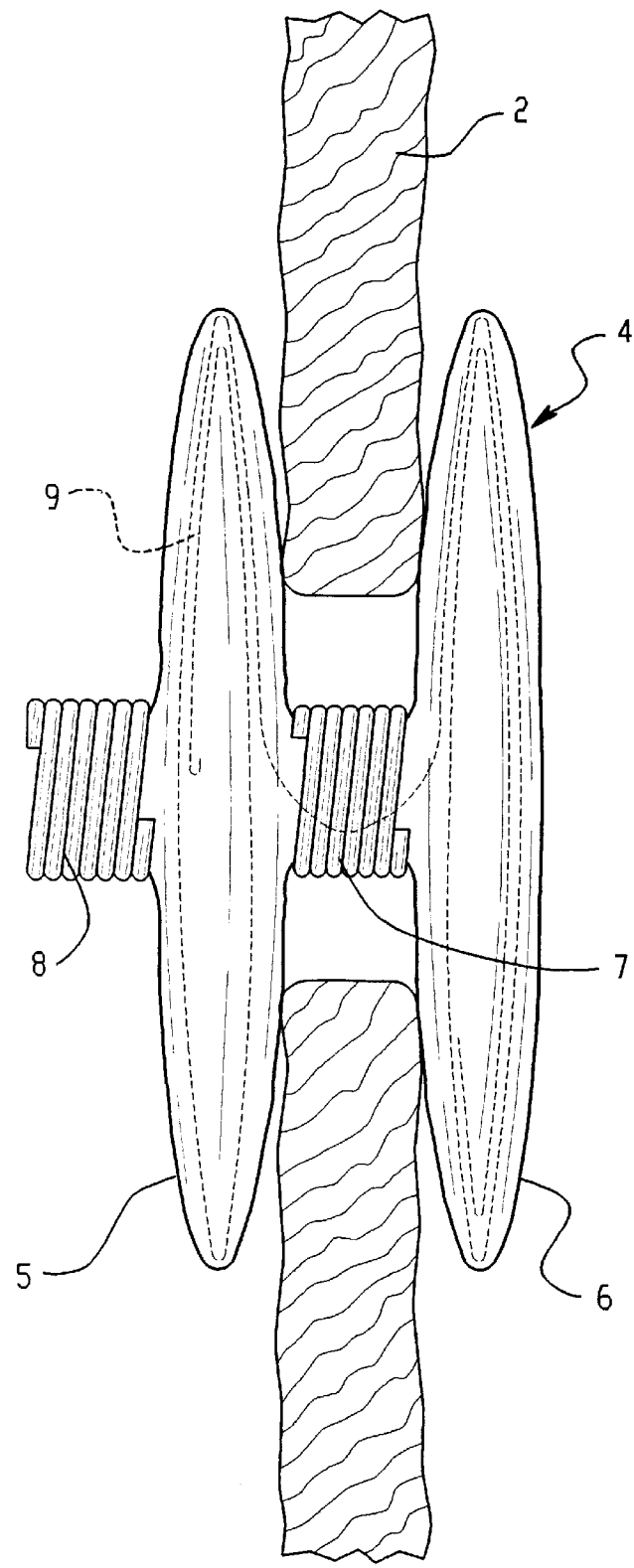
FIG. 2 is a schematic view of an embodiment of the occlusion apparatus of the present invention.

A preferred embodiment of the invention is shown in FIG. 2. The apparatus includes an occlusion bag 4. As seen in FIG. 2, the occlusion bag 4 includes two sacs, one proximal 5 and one distal 6. The sacs 5,6 should be constructed from a thin, porous material. Preferably, the sacs 5,6 are made of nylon mesh screen fabric, for example screen fabric from Industrial Fabrics Corp., or other like fabrics, which are relatively tear and fray resistant. The proximal 5 and distal sacs 6 are connected by suturing the proximal sac 5 on its distal side and the distal sac 6 on its proximal side to a small radio-opaque metallic sac joining connector 7. Furthermore, the proximal sac 5 has another connector opposite this sac joining connector 7. Preferably, this catheter connector 8 is a metallic coil wound to engage the distal tip of delivery catheter.

As further seen in FIG. 2, a single length of pre-programmed super-elastic wire is used to provide a wire support frame 9 for the occlusion bag 4. The wire support frame 9 is preferably a super-elastic formulation of nitinol. The pre-programmed shape of the wire support frame 9 is set by winding the wire around a jig and applying appropriate heat for such wire which is known by one of ordinary skill in the art. The wire support frame's pre-programmed shape is preferably that of two sets of multiple loops. A super-elastic wire formulation of nitinol is preferred over a thermal formulation of nitinol because its temperature dependence is not a significant factor so use of a cold saline bath to prevent deployment during delivery is not necessary. As generally seen in FIG. 2, the wire support frame 9 is disposed within the occlusion bag 4. The wire support frame 9 is not attached to the occlusion bag 4 so the wire support frame 9 can move within the occlusion bag 4 to position the occlusion bag 4 and its sacs 5,6 during deployment.

Figure 3:
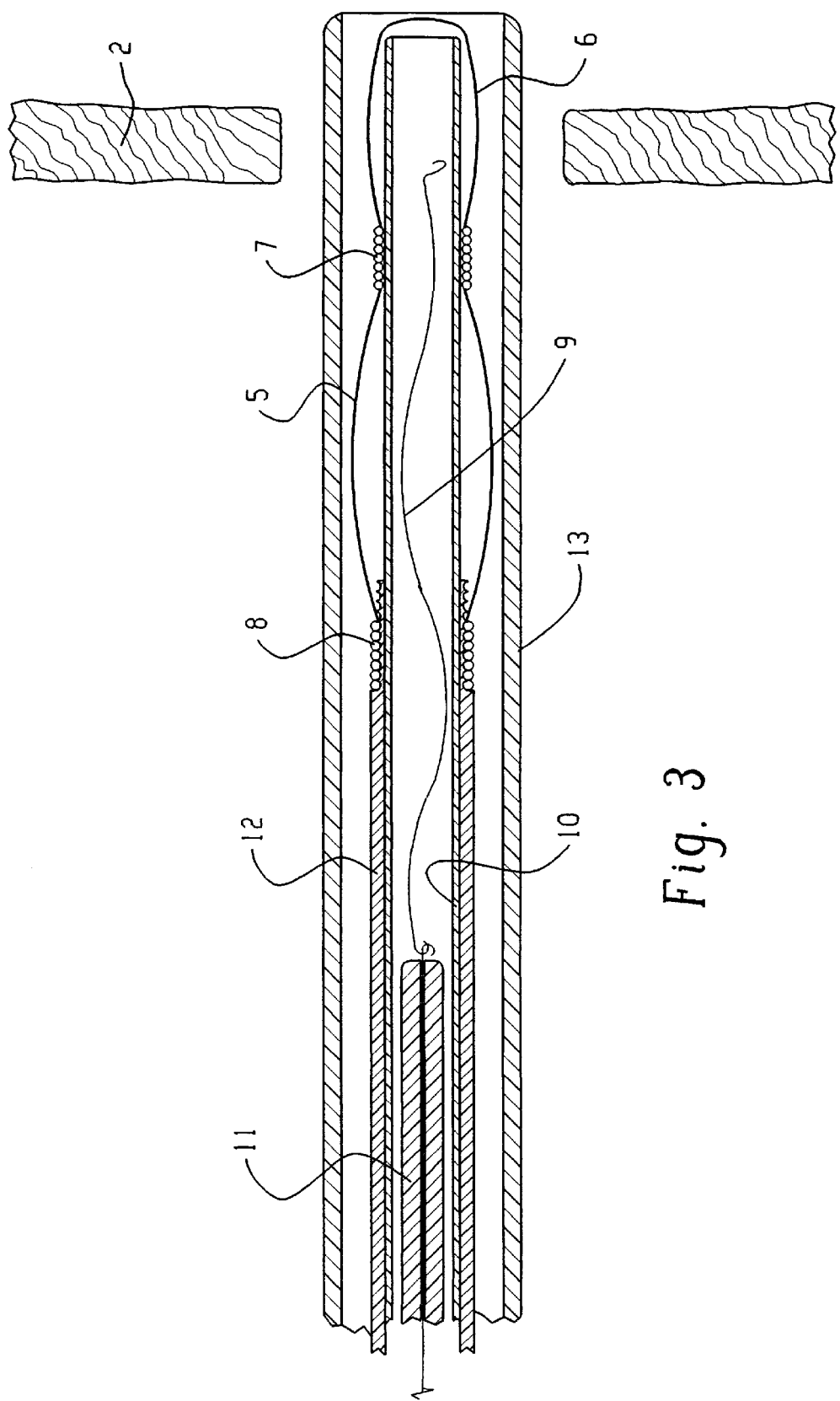
FIG. 3 is an embodiment of the catheter delivery system shown with a schematic cross-sectional view of the occlusion apparatus.

FIG. 3 generally shows a preferred embodiment of the occlusion bag 4, the wire support frame 9 and the catheter deployment system. As shown in FIG. 3, a guide catheter 10 is inserted into the occlusion bag 4. The wire support frame 9 is connected to a release mechanism 11 with this entire assembly then inserted inside the guide catheter 10 for delivery to the aperture 3. The guide catheter 10 is then disposed within a delivery catheter 12 which, in the preferred embodiment, has a threaded distal tip but may include other such engagement mechanisms. The distal tip of the delivery catheter is engaged to a catheter connector 8 located on the proximal sac 5 of the occlusion bag 4. Finally, this entire assembly, composed of the occlusion bag 4, the wire support frame 9, the release mechanism 11, the guide catheter 10 and the delivery catheter 12, are disposed within a delivery sheath 13 for transport to the aperture.

Figure 4:
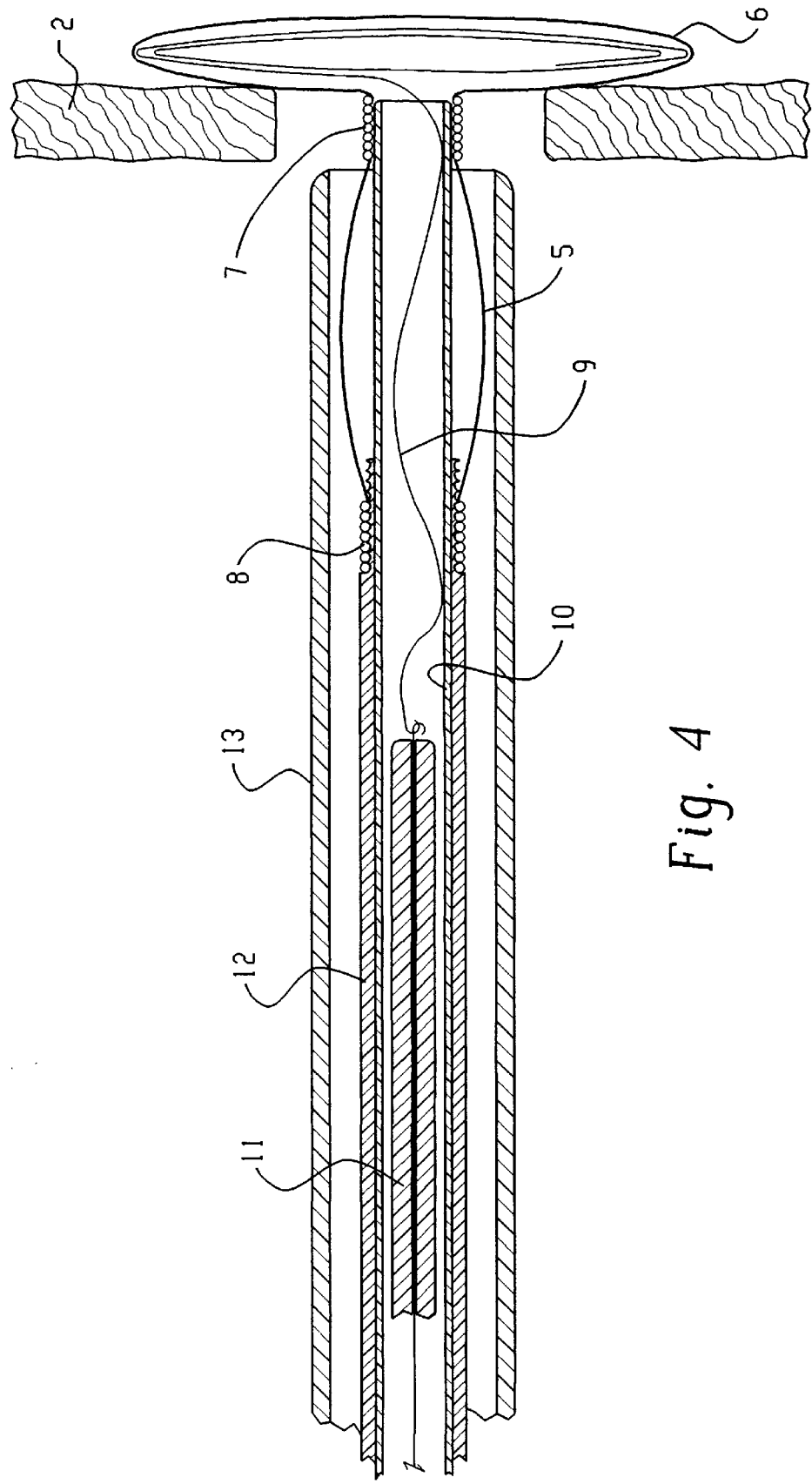
FIG. 4 is a schematic, cross-sectional view of an embodiment of the catheter delivery system as the occlusion apparatus is partially deployed into a distal portion of an atrial septal defect.

FIG. 4 generally shows the initiation of the delivery, deployment and positioning process. The delivery sheath 13 is delivered to the aperture site. Once the delivery sheath 13 has been positioned, the distal sac 6 is advanced past the distal end of the delivery sheath 13 by advancing the guide catheter 10 and delivery catheter 12 as a unit. Once the distal sac 6 is properly positioned, the guide catheter 10 is withdrawn to the mid-portion of the distal sac 6. The guide catheter withdrawal is achieved by removing the guide catheter 10 to a calibrated distance marked on a proximal end of the guide catheter 10. Then, the distal portion of the wire support frame 9 is advanced beyond the distal tip of the guide catheter 10 and into the distal sac 6. As shown in FIG. 4, once the wire support frame 9 is advanced past the distal tip of the guide catheter 10, the distal portion of the wire support frame 9 assumes its pre-programmed configuration preferably consisting of multiple loops. Once the distal portion of the wire support frame 9 is deployed, the entire delivery system is withdrawn slightly so that the distal sac 6 rests against the distal wall of the atrial septum 2.

Figure 5:
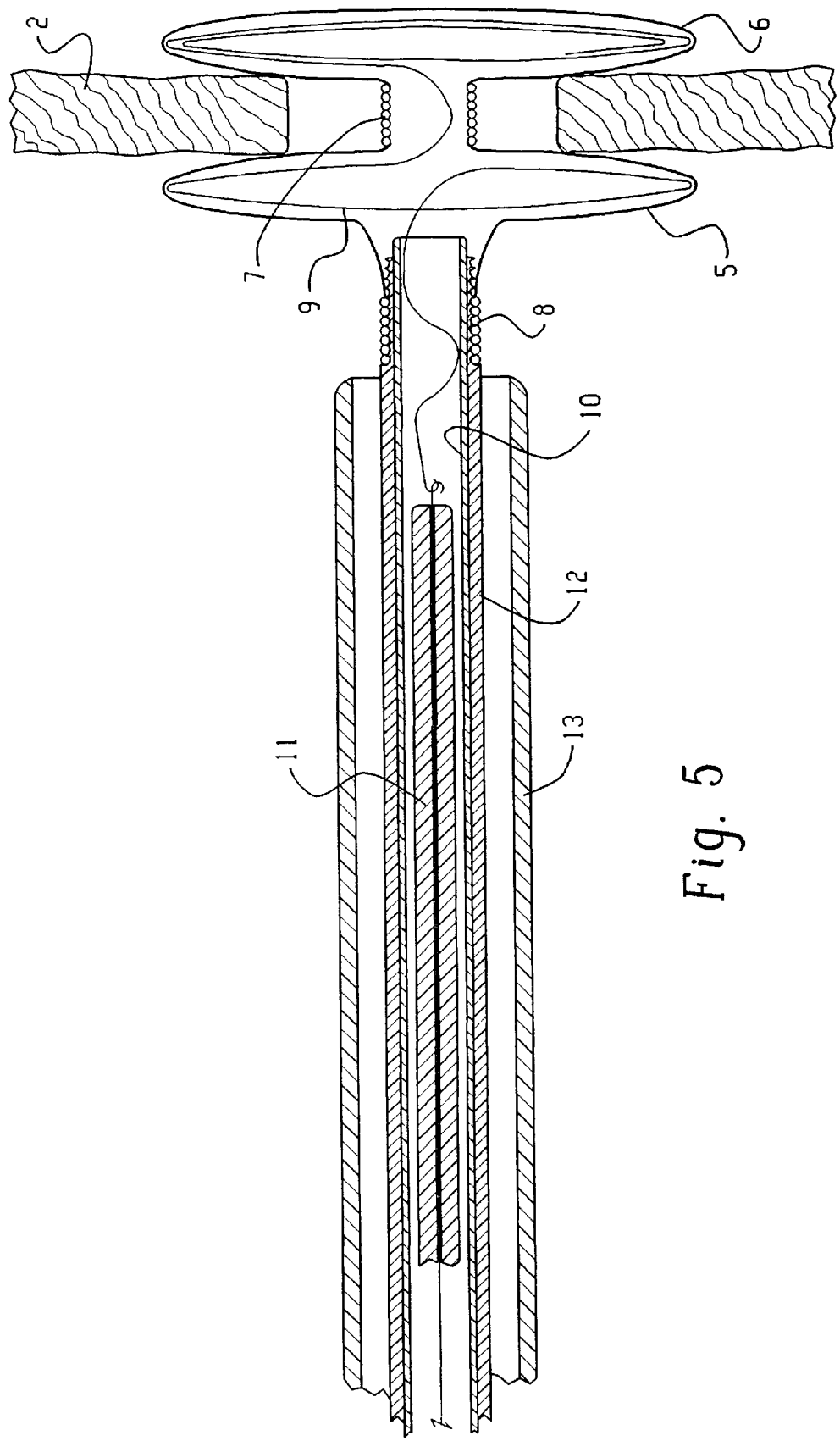
FIG. 5 is a schematic, cross-sectional view of the catheter delivery system as the occlusion apparatus is further partially deployed into a proximal portion of an atrial septal defect.
Figure 6:
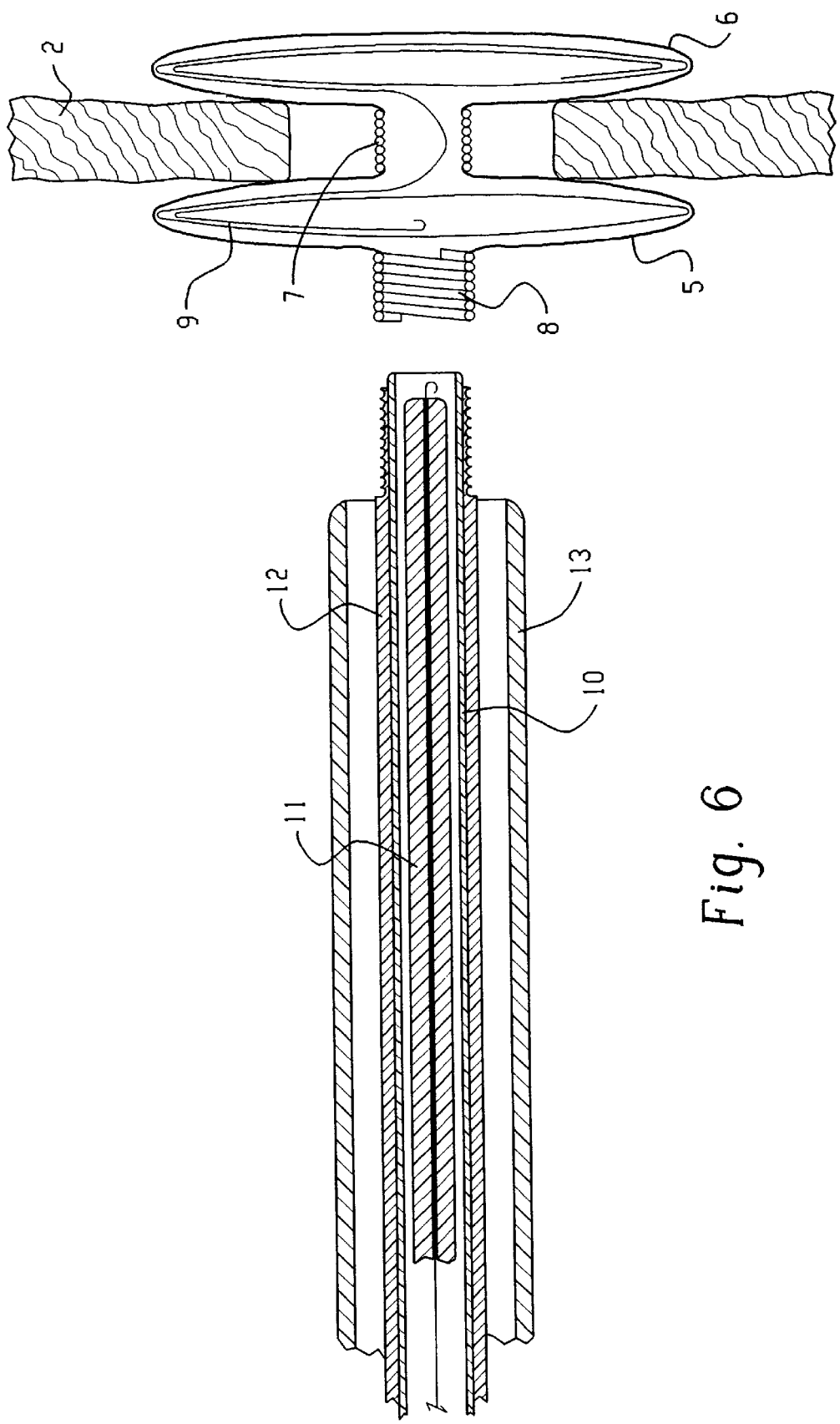
FIG. 6 is a schematic cross-sectional view of an embodiment of the catheter delivery system with the occlusion apparatus has been fully deployed and the catheter delivery system is disengaged therefrom.

As shown in FIG. 5, the delivery sheath 13 is again withdrawn to fully expose the proximal sac 5 of the occlusion bag 4. As with the distal sac 6, the guide catheter 10 is withdrawn to the mid-portion of the proximal sac 5, and the wire support frame 9 advanced and deployed. At this point, the position of the device should be verified either angiographically or by transesopshageal echocardiography. If the position and/or size is not as desired, the entire device can be removed from the aperture by withdrawing the wire and then the bag from the defect. If the device is properly positioned and correctly sized, the release mechanism 11 is activated to release the wire support frame 9 within the occlusion bag 4, the delivery catheter 12 is disengaged from the catheter connector 8 and the guide catheter 10 may be removed. Before the release mechanism is disengaged, the entire occlusion bag 4 and wire support frame 9 may still be removed from the aperture by withdrawing the support wire, and then the still attached delivery catheter 12 from the aperture. Also, even if the wire is disengaged, control over the entire apparatus is maintained. By maintaining control, inadvertent emobilization due to mis-positioning can be avoided. After the wire support frame is disengaged, the device can be held in place if mis-positioned until retrieval by conventional means is effectuated. If however, as shown generally in FIG. 6, the device is properly positioned, the delivery catheter 12 is disengaged from the catheter connector 8 of the proximal sac 5. Once disengaged, the entire delivery system is withdrawn from the aperture with the occlusion device remaining in place to occlude the aperture.

While this invention has been disclosed with reference to specific embodiments, it is apparent that other embodiments and equivalent variations of this invention may be devised without departing from the spirit of the invention and the scope of the claims.

We claim:

1. A method for occluding an aperture within a body surface comprising the steps of:
    a) providing an occlusion bag comprising a proximal sac and a distal sac, said proximal sac connected to said distal sac by a central and said proximal sac having a proximal connector oriented opposite said central connector;
    b) affixing a delivery catheter to said proximal connector of said occlusion bag;
    c) inserting a guide catheter into said delivery catheter;
    d) affixing a proximal end of a super-elastic wire to a release mechanism;
    e) inserting said super-elastic wire and said release mechanism into said guide catheter;
    f) collapsing proximal and distal sacs of said occlusion bag;
    g) inserting a sub-assembly comprising said occlusion bag, said guide catheter, said delivery catheter, said super-elastic wire and said release mechanism, into a delivery sheath;
    h) transporting and positioning said delivery sheath containing said sub-assembly into said aperture;
    i) withdrawing said delivery sheath from said aperture to expose said sub-assembly;
    j) advancing said distal sac of said occlusion bag into a distal portion of said aperture, withdrawing said guide catheter to a mid-portion of said distal sac, advancing a distal portion of said super-elastic wire into said distal sac, and deploying said distal portion of said super-elastic wire within said distal sac of said occlusion bag wherein said super-elastic wire is movably contained within said occlusion bag;
    k) withdrawing said delivery sheath to expose said proximal sac of said occlusion bag, withdrawing said guide catheter to a portion of said proximal sac, advancing a proximal portion of said super-elastic wire into said proximal sac, and deploying said proximal portion of said super-elastic wire within said proximal sac of said occlusion bag;
    l) activating said release mechanism to release said super-elastic wire within said occlusion bag;
    m) withdrawing said guide catheter from said occlusion bag;
    n) disengaging and withdrawing said delivery catheter from said occlusion bag; and
    o) withdrawing said delivery sheath containing said delivery catheter, said guide catheter and said release mechanism.

2. The method of claim 1 wherein activating said release mechanism to release said super-elastic wire causes said super-elastic wire to form a wire frame movably contained within and seperate from said occlusion bag and said wire frame is comprised of multiple loops.

3. The method of claim 1 wherein prior to the step of activating said release mechanism, said super-elastic wire and said occlusion bag may be repositioned within the aperture.

4. An apparatus for occluding an aperture within a body surface comprising:
    a) an occlusion bag comprising a proximal sac, and distal sac, said proximal sac connected to said distal sac by a central connector and said proximal sac having a proximal connector oriented opposite said central connector;

b) a delivery catheter removably attached to said proximal connector of said occlusion bag;

c) a guide catheter inserted into said delivery catheter and movably contained within said occlusion bag;

d) a super-elastic wire having a proximal end and a distal end and insertable into said guide catheter wherein said super-elastic wire is movably contained within said occlusion bag;

e) a release mechanism connected to said proximal end of sid super-elastic wire;

f) said occlusion bag, said delivery catheter, said guide catheter, said super-elastic wire and said release mechanism comprising a sub-assembly; and g) a delivery sheath for containing delivering and deploying said sub-assembly to the aperture.

5. The apparatus of claim 4 wherein said super-elastic wire may be deployed within said occlusion bag as a super-elastic wire frame and the super-elastic wire frame is movably contained within and seperate from said occlusion bag.

6. An apparatus for occluding an aperture within a body surface comprising:

a) an occlusion bag comprising a proximal sac and a distal sac, said proximal sac connected to said distal sac by a central connector and said proximal sac having a proximal connector oriented opposite said central connector; and b) a super-elastic wire frame having two sets of multiple loops wherein said super-elastic wire frame is movably contained within and unattached to said occlusion bag.

7. A method for occluding an aperture within a body surface comprising the steps of:

a) providing an occlusion bag comprising a proximal sac and a distal sac, said proximal sac connected to said distal sac by a central connector and said proximal sac having a proximal connector oriented opposite said central connector;

b) affixing a delivery catheter to said proximal connector of said occlusion bag;

c) inserting a guide catheter into said delivery catheter;

d) affixing a proximal end of a super-elastic wire to a release mechanism;

e) inserting said super-elastic wire and release mechanism into said guide catheter f) collapsing said proximal and distal sacs of said occlusion bag;

g) inserting a sub-assembly comprising said occlusion bag, said guide catheter, said delivery catheter, said super-elastic wire and said release mechanism into a delivery sheath;

h) transporting and positioning said delivery sheath containing said sub-assembly into said aperture;

i) withdrawing said delivery sheath from said aperture to expose said sub-assembly;

j) advancing said distal sac of said occlusion bag into a distal portion of said aperture, withdrawing said guide catheter to a mid-portion of said distal sac, advancing a distal portion of said super-elastic wire into said distal sac, and deploying said distal portion of super-elastic within said distal sac of said occlusion bag;

k) withdrawing said sheath to expose said proximal sac of said occlusion bag, withdrawing said guide catheter to a portion of sid proximal sac, advancing a proximal portion of said super-elastic wire into said proximal sac, and deploying said proximal portion of super-elastic wire within said proximal sac of said occlusion bag and said super-elastic wire is deployed within and unattached to said occlusion bag; and l) repositioning said super-elastic wire and said occlusion bag within the aperature.

\* \* \* \* \*

UNITED STATES PATENT AND TRADEMARK OFFICE
CERTIFICATE OF CORRECTION

PATENT NO. : 5,861,003
DATED : Jan. 19, 1999
INVENTOR(S) : Latson, et al.

It is certified that error appears in the above-identified patent and that said Letters Patent is hereby corrected as shown below:

Column 6, line 6, after "central" insert --connector--.

Signed and Sealed this

Eighteenth Day of May, 1999

Attest:

Q. TODD DICKINSON

*Attesting Officer*   *Acting Commissioner of Patents and Trademarks*